United States Patent
Yadav et al.

(10) Patent No.: US 12,285,029 B2
(45) Date of Patent: Apr. 29, 2025

(54) MICROBIAL METHOD FOR PRODUCTION OF PROTEIN ISOLATE/CONCENTRATE FROM OILSEED CAKES/MEALS

(71) Applicant: Indian Council of Agricultural Research, New Delhi (IN)

(72) Inventors: Deep Narayan Yadav, Ludhiana (IN); Sangita Bansal, New Delhi (IN); Rajesh Kumar Singh, Ludhiana (IN); Shyam Narayan Jha, New Delhi (IN)

(73) Assignee: Indian Council of Agricultural Research, New Delhi (IN)

( * ) Notice: Subject to any disclaimer, the term of this patent is extended or adjusted under 35 U.S.C. 154(b) by 1059 days.

(21) Appl. No.: 17/258,088

(22) PCT Filed: Mar. 27, 2020

(86) PCT No.: PCT/IN2020/050287
§ 371 (c)(1),
(2) Date: Jan. 5, 2021

(87) PCT Pub. No.: WO2020/202185
PCT Pub. Date: Oct. 8, 2020

(65) Prior Publication Data
US 2021/0282428 A1 Sep. 16, 2021

(30) Foreign Application Priority Data
Mar. 29, 2019 (IN) .............................. 201911012570

(51) Int. Cl.
| | | |
|---|---|---|
| *A23J 1/12* | (2006.01) | |
| *A23J 1/14* | (2006.01) | |
| *A23J 3/16* | (2006.01) | |
| *C12N 1/20* | (2006.01) | |
| *C12P 21/00* | (2006.01) | |
| *C12R 1/225* | (2006.01) | |
| *C12R 1/23* | (2006.01) | |

(52) U.S. Cl.
CPC .............. *A23J 1/125* (2013.01); *A23J 1/142* (2013.01); *A23J 1/148* (2013.01); *A23J 3/16* (2013.01); *C12N 1/20* (2013.01); *C12P 21/00* (2013.01); *C12R 2001/225* (2021.05); *C12R 2001/23* (2021.05)

(58) Field of Classification Search
CPC .. A23J 1/125; A23J 1/142; A23J 1/148; A23J 3/16; A23J 1/14; A23J 3/14; C12N 1/20; C12P 21/00; C12R 2001/225; C12R 2001/23
See application file for complete search history.

(56) References Cited

U.S. PATENT DOCUMENTS 10,136,661 B2    11/2018   Kang et al.
2017/0238590 A1*   8/2017   Bansal-Mutalik ...... A23J 1/148

FOREIGN PATENT DOCUMENTS

| WO | WO-2013/013949 A1 | 1/2013 |
| WO | WO-2014/147068 A1 | 9/2014 |
| WO | WO-2015/170855 A1 | 11/2015 |

OTHER PUBLICATIONS

Amadou et al. (Year: 2010).*
Medeiros (Year: 2015).*
Mukherjee et al. (Year: 2016).*
Sharma et al. (2014, J Food Sci Technol, DOI 10.1007/s13197-013-0959-1) {herein Sharma} (Year: 2014).*
Miami Water & Air (2024, https://www.miamiwaterandair.com/does-soft-water-affect-the-ph-balance-of-water/#:~:text=Most) {herein Miami Water & Air}. (Year: 2024).*
Mederios (2015, Improving the nutritional value of soybean meal through fermentation using newly isolated bacteria, atrium.lib. uoguelph.ca) {herein Mederios}. (Year: 2015).*
Vartoukian et al. (2010, minireview, DOI:10.1111/j.1574-6968.2010.02000.x) {herein Vartoukian}. (Year: 2010).*
Indian First Examination Report for IN 201911012570, dated Jun. 9, 2021, 7 pgs.
U. Garba, et al., "Protein Isolates: Production, Functional Properties and Application", Int J. Cur. Res. Rev., Feb. 2014, vol. 6, No. 3, pp. 35-45.
International Search Report & Written Opinion for PCT/IN2020/050287 dated Aug. 27, 2020, 11 pages.

* cited by examiner

*Primary Examiner* — Paul J Holland
*Assistant Examiner* — Erica Nicole Jones-Foster
(74) *Attorney, Agent, or Firm* — Blank Rome LLP

(57) ABSTRACT

Alkaline extraction followed by acid precipitation or ultrafiltration method for preparation of protein isolates from oilseeds cakes/meals is followed. The strong alkaline and acidic conditions alter the functional properties of the protein, which adversely affects its quality. The present invention provides a microbial based process to produce protein isolates/concentrates from oilseed cakes/meals or from other similar type of sources either plant or animal origin without addition of strong or diluted acid. The protein is extracted in aqueous media or alkaline aqueous media with or without containing specified salt for specified duration. The extract is centrifuged, mixed with known microbial culture (the process is not limited to the particular strain) and incubated at particular temperature and duration. The precipitated protein is recovered and dried to get protein isolates/concentrates. The process is convertible to purely chemical free process as extraction of protein in potable water, precipitation of protein using microbial culture followed by drying.

12 Claims, 1 Drawing Sheet

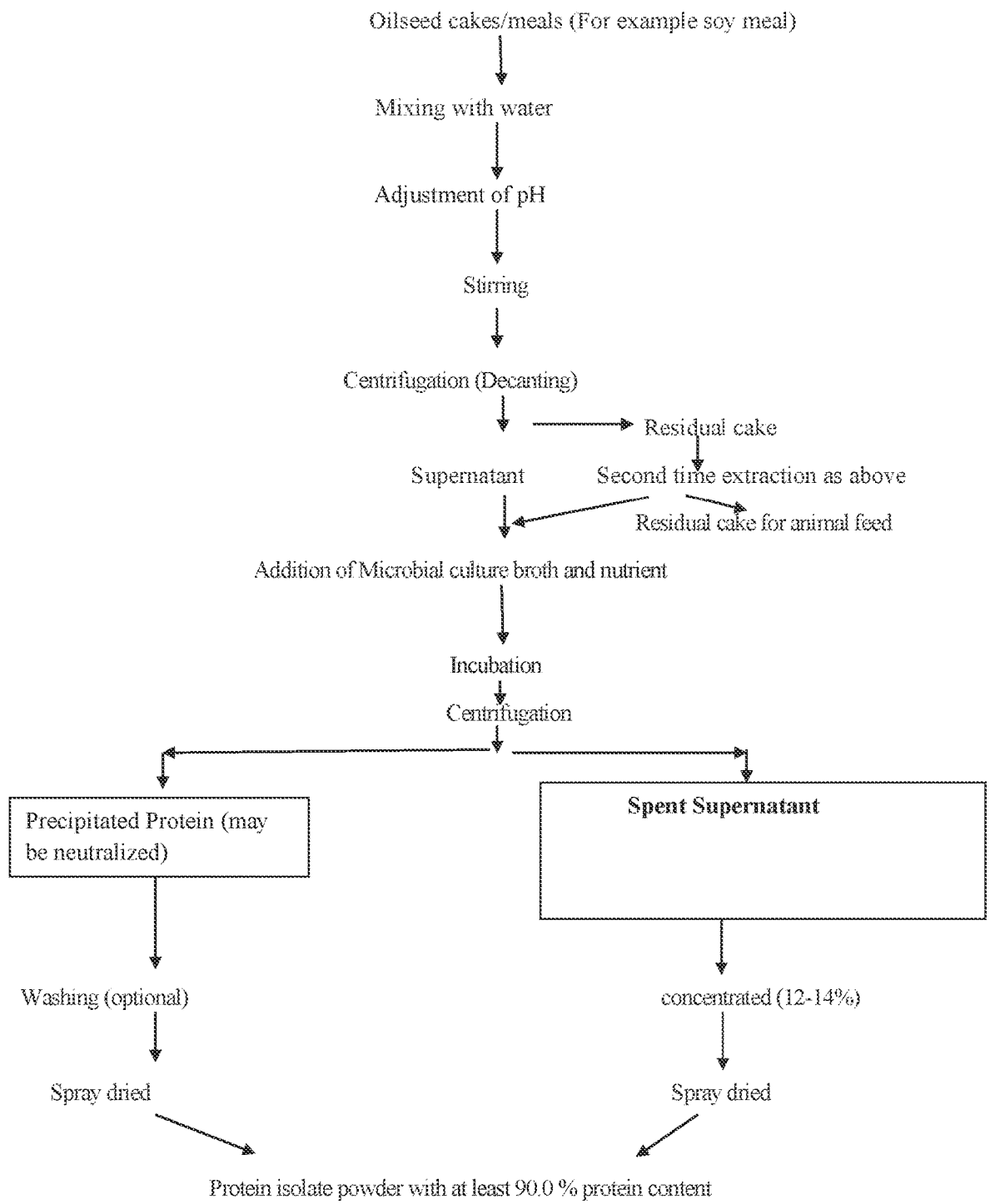

MICROBIAL METHOD FOR PRODUCTION OF PROTEIN ISOLATE/CONCENTRATE FROM OILSEED CAKES/MEALS

RELATED APPLICATIONS

This application is a national phase of PCT/IN2020/050287, filed on Mar. 27, 2020, which claims the benefit of Indian Application No. 201911012570, filed on Mar. 29, 2019. The entire contents of these applications are hereby incorporated by reference.

FIELD OF THE INVENTION

The present invention relates to a microbial process for the production of protein isolate/concentrate from aqueous extract of oilseed meal/flour. The present disclosure also relates to a probiotic protein isolate/concentrate prepared from de-oiled meal/flour by said microbial process and is having lower anti-nutritional factors.

BACKGROUND OF THE INVENTION

Worldwide, alkaline extraction followed by acid precipitation or ultrafiltration method for preparation of protein isolates from oilseeds cakes/meals is followed. The strong alkaline and acidic conditions alter the functional properties of the protein, which adversely affects its quality. In contrast, the present disclosure provides a microbial process which does not require addition of acid for precipitation of the protein. Hence, the present disclosure provides a method that not only maintains the native quality of protein and provides about 3.0-3.5% higher yield of protein as compared to alkali extraction and acid precipitation methods known in the art. The method of the present disclosure is also convertible into purely chemical free process by extracting the protein using potable water (neutral pH) and precipitation by the novel microbial culture. Further, the un-precipitated protein present in the supernatant produced during the course of precipitation of protein using microbial culture can be recovered by ultra-filtration of suitable pore size. Since, this supernatant had very low solids content, hence, minimizes the problem of frequent membrane fouling caused due to higher solids content in supernatant during concentration by membrane processing.

India produces about 17 mT de-oiled cakes/meals comprising 7.4 and 1.6 mT soymeal and groundnut cake, respectively containing 35-50% protein. At present, these are utilized as animal feed in India or exported. The process of the present disclosure provides a simple, cost effective and useful method for manufacturing protein isolate/concentrate of high quality with competitive cost of production by utilizing indigenous raw materials.

Some laboratory level efforts have been made in the past to isolate proteins from oilseeds. Nath and Rao (1981) compared protein isolate from guar meal prepared at laboratory scale with soy protein isolate. Sastry & Subramanian (1984) extracted protein concentrate from de-hulled sunflower kernels. Venktesh & Prakash (1993) evaluated functional properties of sunflower proteins. Sadegi et al (2006) studied the effect of steam treatment on anti-nutrients content of protein isolate obtained from de-hulled- and de-oiled mustard. Radha et al (2007) prepared and characterized protein hydrolysate from oilseeds flour mixture. Bandyopadhyay & Ghosh (2002) prepared and characterized papain-modified sesame protein isolate. Improvement in functional properties of protein isolate (prepared by alkali extraction and acid precipitation) from commercial groundnut cake through enzymatic hydrolysis was reported by Yadav et al, 2014. They also studied the effect of process (alkali extraction and acid precipitation) parameters on the preparation of protein isolates from commercial sunflower cake using micro-filtration and reported 55% recovery of total protein (Yadav et al, 2016).

Extraction and characterization of proteins from different de-oiled cakes/meals is well known in the art. Processes for protein isolate extraction from soy meal and peanut cake is comprehensively reported (Liu et al 2001, Barker, et al 2002 & 2003, Yu et al 2007, Wu et al 2007). Barker, et al (2002 & 2003) patented the process for production of protein isolates from oilseeds. The process was based on alkali extraction and acid (Diluted HCL) precipitation. They also patented process for production of mustard seed protein isolate in 2009. Shallo et al (2001) prepared soy protein concentrates through ultra-filtration with reduced level of phytic acid and 17-26% higher protein recovery. Xu et al (2003) produced protein isolate (<0.5% phytate and glucosinolates free) from mustard meal by membrane process. Pickardt et al (2009) optimized acidic extraction process for sunflower meal. Ivanova et al (2014) studied functional properties of the protein isolates from industrial sunflower meal. Khalil (2001) studied biochemical and technological parameters of guar protein isolate. Karagianni et al (2010) patented a composition of guar protein extract with other materials for the treatment of surfaces.

The major drawback of the known precipitation methods for preparation of protein isolates is that the said methods are chemical based processes and comprise alkali and acid treatment, which deteriorate the protein quality. Hence, there is an urgent need for a process for the preparation of protein isolates from de-oilseed flour/meals without affecting the quality of protein. The present application provides a solution to aforesaid problem and provides a microbial process for the isolation of proteins from de-oilseed flour/meals, which does not require any added acid in order to precipitate the protein and maintain native quality of protein with same amount or better yield of protein as compared to alkali extraction and acid precipitation methods known in the art. The present disclosure also provides a purely non-chemical method for the extraction of protein isolates, using potable water (neutral pH) and the precipitation of protein isolates by the microbial culture. The process of the present disclosure yield protein of superior quality. The process of the present disclosure also minimizes the problem of frequent membrane fouling caused due to higher solids content. The process of the present disclosure also minimizes the number of steps for protein isolate preparation by precipitating and hydrolysing the proteins simultaneously. Hence, the present disclosure provides a simple, cost effective and economical microbial process for the isolation of proteins from de-oilseed flour/meal.

OBJECTIVE OF THE INVENTION

The primary object of the present disclosure is to develop a microbial process for the preparation of protein isolate/concentrate from de-oilseed flour/meal.

Another object of the present disclosure is to provide a non-chemical process for the preparation of protein isolates from de-oilseed flour/meal to yield protein of superior quality.

Yet another object of the present disclosure is to provide a probiotic protein isolate/concentrate prepared by the microbial process and is having lower anti-nutritional factors.

Advantages

The microbial process of the present disclosure is unique as it does not require any acid treatment to precipitate the protein. Hence, maintains almost native quality of protein with same or better yield of protein as reported by alkali extraction and acid precipitation method, known in the art.

The method of the present disclosure is also convertible into purely chemical free process by extracting the protein using potable water (neutral pH) and precipitation by the novel microbial culture.

The un-precipitated protein present in the supernatant produced during the course of precipitation of protein using microbial culture is also recovered by ultrafiltration of suitable pore size. Hence, the yield of protein isolates is higher.

Since the supernatant after the extraction of protein isolates had very low solids content, hence the process of the present disclosure also minimizes the problem of frequent membrane fouling caused due to higher solids content in supernatant during protein isolate production by membrane processing.

Minimizes the number of steps like stepwise precipitation in alkali/acid precipitation for protein isolate preparation.

Minimizes the cost of production.

SUMMARY OF THE INVENTION

Existing methods for the production of protein isolates from oilseed cakes/meals comprises alkaline extraction followed by acid precipitation or ultrafiltration method. The major limitation of said processes is strong alkaline and acidic conditions alter the functional properties of the protein, which adversely affects its quality. The present disclosure overcomes the aforesaid problem and provides a solution to strong alkaline and acidic conditions used during the course of protein isolate production.

In accordance with the present invention, there is provided a microbial process for the preparation of protein isolate/concentrate from d-oiled meal/flour, said process comprising the steps of:
a) adding potable water to de-oiled meal/flour to form slurry;
b) stirring the slurry of step (a) at a temperature in the range of 30 to 70° C. for 1 to 2 hours followed by centrifugation to obtain supernatant and residual cake;
c) repeating step (a) and (b) with residual cake of step (b) to obtain supernatant;
d) adding microbial culture and nutrient media to the supernatant and allow it to incubate at a temperature in the range of 37 to 43° C. for about 10 to 20 hours in an incubator/fermenter;
e) centrifuging the resulting mixture of step (d) to recover the precipitated protein and spent supernatant;
f) drying the precipitated protein of step (e) to obtain protein isolate/concentrate.

In an embodiment of the present disclosure, there is provided a microbial process for the preparation of protein isolate/concentrate from de-oiled meal/flour, wherein in step (a) salt, base, potable water and de-oiled meal/flour are combined to form alkaline slurry having a pH of 9 to 10.

In an embodiment of the present disclosure, there is provided a microbial process for the preparation of protein isolate/concentrate from de-oiled meal/flour, wherein the centrifugation is carried out at 6000-8000 rpm for 10-30 minutes.

In an embodiment of the present disclosure, there is provided a microbial process for the preparation of protein isolate/concentrate from de-oiled meal/flour, wherein the microbial culture is acid producing bacteria selected from the group consisting of *Lactobacilli. Streptococci* and a combination thereof.

In an embodiment of the present disclosure, there is provided a microbial process for the preparation of protein isolate/concentrate from de-oiled meal/flour, wherein the microbial culture comprises of *Lactobacillus fermentum* and *Lactobacillus acidophilus* in a concentration of 1-10 ml/100 ml supernatant containing $1\times10^6$-$1\times10^8$ cfu/ml.

In an embodiment of the present disclosure, there is provided a microbial process for the preparation of protein isolate/concentrate from de-oiled meal/flour, wherein the spent supernatant obtained in step (e) is concentrated up to 12-14% solid content using ultra-filtration (10 kDa) to recover un-precipitated proteins.

In an embodiment of the present disclosure, there is provided a microbial process for the preparation of protein isolate/concentrate from de-oiled meal/flour, wherein the spent supernatant obtained in step (e) is used as an inoculum of fresh extract at the same rate in place of pure microbial culture.

In an embodiment of the present disclosure, there is provided a microbial process for the preparation of protein isolate/concentrate from de-oiled meal/flour, wherein the protein isolate/concentrate is having a protein content of at least 90% (db).

In an embodiment of the present disclosure, there is provided a microbial process for the preparation of protein isolate/concentrate from de-oiled meal/flour, wherein the de-oiled meal/flour is derived from oilseed selected from the group consisting of groundnut, soybean, sunflower, mustard, sesame, other oilseeds or any other protein source of plant/animal origin.

In an embodiment of the present disclosure, there is provided a microbial process for the preparation of protein isolate/concentrate from de-oiled meal/flour, wherein the protein isolate/concentrate is a dried proteinaceous powder.

In an embodiment of the present disclosure, there is provided a microbial process for the preparation of protein isolate/concentrate from de-oiled meal/flour, wherein the proteinaceous powder is a probiotic protein powder.

In an embodiment of the present disclosure, there is provided a microbial process for the preparation of protein isolate/concentrate from de-oiled meal/flour, wherein the protein isolate/concentrate obtained is having lower anti-nutritional factors like trypsin inhibitor, phytic acids.

In an embodiment of the present disclosure, there is provided a microbial process for the preparation of protein isolate/concentrate from de-oiled meal/flour, wherein the water solubility of protein isolate/concentrate increases from 45% to 75% when temperature is increased from 20° C. to 60° C.

In an embodiment of the present disclosure, there is provided a microbial process for the preparation of protein isolate/concentrate from de-oiled meal/flour, said process comprising:
(a) adding water to de-oiled meal/flour to form slurry;

(b) stirring the slurry of step (a) at a temperature in the range of about 30 to 70° C. for about 1 to 2 hours followed by centrifugation to obtain supernatant and residual cake;

(c) optionally repeating steps (a) and (b) with residual cake of step (b) to obtain supernatant;

(d) adding microbial culture and nutrient media to the supernatant and incubating at a temperature in the range of about 37 to 43° C. for about 10 to 20 hours;

(e) centrifuging the resulting mixture of step (d) to recover the precipitated protein and spent supernatant;

(f) drying the precipitated protein of step (e) to obtain protein isolate/concentrate.

In an embodiment of the present disclosure, there is provided a protein isolate/concentrate prepared from de-oiled meal/flour by a process as described herein.

In an embodiment of the present disclosure, there is provided a protein isolate/concentrate prepared from d-oiled meal/flour by a process as described herein, wherein the protein isolate/concentrate is isolated from groundnut, soybean, sunflower, mustard, sesame, other oilseeds or any other protein source of plant/animal origin.

In an embodiment of the present disclosure, there is provided a protein isolate/concentrate prepared from d-oiled meal/flour by a process as described herein, wherein the protein isolate/concentrate is a soybean protein isolate/concentrate.

In an embodiment of the present disclosure, there is provided a protein isolate/concentrate prepared from d-oiled meal/flour by a process as described herein, wherein the soybean protein isolate/concentrate is having a protein content of at least 90% (db); moisture content of 4.12%; probiotic count of $12 \times 10^{11}$ cfu/ml; phytic acid content of less than 1.85 g/100 g and trypsin inhibitor units of less than 3600 TIU/g.

In an embodiment of the present disclosure, there is provided a protein isolate/concentrate prepared from d-oiled meal/flour by a process as described herein, wherein the soybean protein isolate/concentrate is having a water absorption capacity of 3.6-3.9 g/g, degree of hydrolysis in the range of 12.0-14.0% and water solubility in the range of 45-80%.

BRIEF DESCRIPTION OF THE DRAWING

FIG. 1 is a schematic diagram of a microbial process for the preparation of protein isolate/concentrate according to one embodiment of the invention as applied to soyameal but also generally to other oil seed meals.

DETAILED DESCRIPTION OF THE INVENTION

Those skilled in the art will be aware that the present disclosure is subject to variations and modifications other than those specifically described. It is to be understood that the present disclosure includes all such variations and modifications. The disclosure also includes all such steps of the process, features of the product, referred to or indicated in this specification, individually or collectively, and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

The present disclosure is not to be limited in scope by the specific embodiments described herein, which are intended for the purposes of exemplification only. Functionally equivalent products and methods are clearly within the scope of the disclosure, as described herein.

In accordance with the present invention, there is provided a microbial process for the preparation of protein isolate/concentrate from de-oiled meal/flour, said process comprising the steps of:

a) adding potable water to de-oiled meal/flour to form slurry;

b) stirring the slurry of step (a) at a temperature in the range of 30 to 70° C. for 1 to 2 hours followed by centrifugation to obtain supernatant and residual cake;

c) repeating step (a) and (b) with residual cake of step (b) to obtain supernatant;

d) adding microbial culture nutrient media to the supernatant and allow it to incubate at a temperature in the range of 37 to 43° C. for about 10 to 20 hours in an incubator/fermenter;

e) centrifuging the resulting mixture of step (d) to recover the precipitated protein and spent supernatant;

f) drying the precipitated protein of step (e) to obtain protein isolate/concentrate.

In an embodiment, the present disclosure provides a microbial process for the preparation of protein isolate/concentrate from de-oiled meal/flour, wherein in step (a) salt, base, potable water and de-oiled meal/flour are combined to form alkaline slurry having a pH of 9 to 10.

In an embodiment, the present disclosure provides a microbial process for the preparation of protein isolate/concentrate from de-oiled meal/flour, wherein the centrifugation is carried out at 6000-8000 rpm for 10-30 minutes.

In an embodiment, the present disclosure provides a microbial process for the preparation of protein isolate/concentrate from de-oiled meal/flour, wherein the microbial culture is acid producing bacteria selected from the group consisting of *Lactobacilli, Streptococci* etc. and a combination thereof.

Use of microbes for production of protein isolates/concentrates from de-oilseeds flour/meals or similar type of material has not been yet disclosed. Further, the method of the present disclosure comprises a novel bacterial strain *Lactobacillus fermentum* strains BBE4, isolated from a food sample in the laboratory of applicant institute (ICAR-Central Institute of Post-harvest Engineering and technology) for precipitating the protein from aqueous extract of de-oiled meal/flour (pH range: 6.0-12.0). The above-mentioned strain has been registered (MTCC No: 12061) and deposited with MTCC, IMTECH, Chandigarh, India on Sep. 20, 2019 in compliance with Budapest treaty and its 16S rDNA sequence has been registered with NCBI vide GenBank vide accession number KF974325. After isolation, the probiotic potential of the isolate i.e., tolerance towards bile, gastric juice, low pH and antibiotic sensitivity was tested. *Lactobacillus fermentum* strain BBE4 was able to survive at a low pH 4 showing survival percentage 83% thus had a good bile resistance property and good tolerance to gastric juice even after exposure for 24 hours. However, the process of the present application is not limited to a particular strain, but may include other acid producing bacteria such as *Lactobacilli, Streptococci* etc. The process is also convertible to purely chemical free process as extraction of protein in potable water, precipitation of protein using microbial culture followed by drying.

In an embodiment, the present disclosure provides a microbial process for the preparation of protein isolate/concentrate from de-oiled meal/flour, wherein the microbial culture comprises of *Lactobacillus fermentum* and *Lactobacillus acidophilus* in a concentration of 1-10 ml/100 ml supernatant containing $1 \times 10^6$-$1 \times 10^8$ cfu/ml.

The spent supernatant obtained contains residual/unprecipitated proteins and are extracted by ultrafileration. In an embodiment, the present disclosure provides a microbial process for the preparation of protein isolate/concentrate from de-oiled meal/flour, wherein the spent supernatant obtained in step (e) is concentrated up to 12-14% solid content using ultra-filtration (10 kDa) to recover un-precipitated proteins.

The spent supernatant obtained may be neutralised and is reusable. In an embodiment, the present disclosure provides a microbial process for the preparation of protein isolate/concentrate from de-oiled meal/flour, wherein the spent supernatant obtained in step (e) is used as an inoculum of fresh extract at the same rate in place of pure microbial culture.

The present disclosure provides a microbial process for extracting protein isolate/concentrate in good yield. In an embodiment, the present disclosure provides a microbial process for the preparation of protein isolate/concentrate from de-oiled meal/flour, wherein the protein isolate/concentrate is having a protein content of at least 90% (db).

The protein isolate/concentrate prepared by the process of the present disclosure is of superior quality in comparison to that obtained by acid precipitation method known in the art. The protein isolates prepared by the present microbial process is characterised for various quality parameters and the results obtained are shown in table 1 below:

TABLE 1

Comparative quality parameters of soybean protein isolates produced by Acid (HCL) precipitation and process (microbial) of the present invention

| PARAMETERS | Acid (HCL) Precipitation | Microbial method (present process) |
| --- | --- | --- |
| Moisture % | 4.20 | 4.12 |
| Total Ash % | 4.24 | 4.20 |
| Protein (% db) | 90 | 90.00 |
| Yield (% total soy meal) | 31.30 | 34.60 |
| Bulk Density (g/mL) | 0.33 | 0.32 |
| Solubility in distilled water at 20° C.(%) | 30.3 | 45.0 |
| Solubility in distilled water at 40° C.(%) | 32 | 68 |
| Solubility in distilled water at 60° C.(%) | 49 | 75 |
| Water absorption capacity (g/g) | 2.16 | 3.98 |
| Oil absorption capacity (g/g) | 2.78 | 2.64 |
| Degree of hydrolysis (%) | 6.22 | 12.78 |
| Probiotic count | Nil | $12 \times 10^{11}$ cfu/ml |
| Phytic acid content (g/100 g) | 3.65 | 1.85 |
| Trypsin (TIU/ml) (by Kakade et al 1972) | 3.12 (7800 TIU/g) | 1.44 (3600 TIU/g) |
| Aflatoxin | 3.00 ppb | 3.00 ppb |

From the obtained results, it is concluded that the process of the present disclosure provides protein isolates in higher yield ad of superior quality. The protein isolate/concentrate prepared by the present process is having lower anti-nutritional factors like trypsin inhibitor, phytic acids as compared to protein isolates prepared by acid precipitation method, as shown in table 1 above.

Oilseeds are good source of protein and are used for the preparation of protein isolates. In an embodiment, the present disclosure provides a microbial process for the preparation of protein isolate/concentrate from de-oiled meal/flour, wherein the de-oiled meal/flour is derived from oilseed selected from the group consisting of groundnut, soybean, sunflower, mustard, sesame, other oilseeds or any other protein source of plant/animal origin.

The protein isolate/concentrate of the present disclosure is obtained in various forms. In an embodiment, the present disclosure provides a microbial process for the preparation of protein isolate/concentrate from de-oiled meal/flour, wherein the protein isolate/concentrate is a dried proteinaceous powder.

In an embodiment, the present disclosure provides a microbial process for the preparation of protein isolate/concentrate from de-oiled meal/flour, wherein the proteinaceous powder obtained is a probiotic protein powder.

In an embodiment, the present disclosure provides a microbial process for the preparation of protein isolate/concentrate from de-oiled meal/flour, wherein the protein isolate/concentrate obtained is having lower anti-nutritional factors like trypsin inhibitor, phytic acids.

In an embodiment of the present disclosure, there is provided a microbial process for the preparation of protein isolate/concentrate from de-oiled meal/flour, wherein the water solubility of protein isolate/concentrate increases from 45% to 75% when temperature is increased from 20° C. to 60° C.

In an embodiment of the present disclosure, there is provided a microbial process for the preparation of protein isolate/concentrate from de-oiled meal/flour, said process comprising:

(a) adding water to de-oiled meal/flour to form slurry;
(b) stirring the slurry of step (a) at a temperature in the range of about 30 to 70° C. for about 1 to 2 hours followed by centrifugation to obtain supernatant and residual cake;
(c) optionally repeating steps (a) and (b) with residual cake of step (b) to obtain supernatant;
(d) adding microbial culture and nutrient media to the supernatant and incubating at a temperature in the range of about 37 to 43° C. for about 10 to 20 hours;
(e) centrifuging the resulting mixture of step (d) to recover the precipitated protein and spent supernatant;
(f) drying the precipitated protein of step (e) to obtain protein isolate/concentrate.

In an embodiment of the present disclosure, there is provided a protein isolate/concentrate prepared from d-oiled meal/flour by a process as described herein.

In an embodiment of the present disclosure, there is provided a protein isolate/concentrate prepared from de-oiled meal/flour by a process as described herein, wherein the protein isolate/concentrate is isolated from groundnut, soybean, sunflower, mustard, sesame, other oilseeds or any other protein source of plant/animal origin.

In an embodiment of the present disclosure, there is provided a protein isolate/concentrate prepared from de-oiled meal/flour by a process as described herein, wherein the protein isolate/concentrate is a soybean protein isolate/concentrate.

In an embodiment of the present disclosure, there is provided a protein isolate/concentrate prepared from de-oiled meal/flour by a process as described herein, wherein the soybean protein isolate/concentrate is having a protein content of at least 90% (db); moisture content of 4.12%; probiotic count of $12\times10^{11}$ cfu/ml; phytic acid content of less than 1.85 g/100 g and trypsin inhibitor units of less than 3600 TIU/g.

In an embodiment of the present disclosure, there is provided a protein isolate/concentrate prepared from de-oiled meal/flour by a process as described herein, wherein the soybean protein isolate/concentrate is having a water absorption capacity of 3.6-3.9 g/g, degree of hydrolysis in the range of 12.0-14.0% and water solubility in the range of 45-80%.

Following non-limiting examples are given by way of illustration for specific embodiments thereof and therefore should not be construed to limit the scope of the invention.

Example 1

This example illustrates the preparation of a protein isolate from solvent extracted soyabean meal in accordance with one embodiment of the invention using the procedure of FIG. 1.

One kg hexane extracted untoased soya meal (Protein 50.0 g/100 g soy meal) is mixed with 10 litre of potable water containing 0.15 g/100 ml of NaCl (Sodium Chloride) to form slurry. pH of the slurry was adjusted to alkaline conditions (9.5) by adding 1 N NaOH (sodium hydroxide). The mixture was stirred for about 80 minutes at about 70° C. The slurry was centrifuged at about 7000 rpm for about 20 minutes and supernatant was collected (8.5 litre). Microbial culture broth comprising *Lactobacillus fermentum* BBE4 and *Lactobacillus acidophilus* NCDC No 016 @ 1 ml/100 ml supernatant containing $1\times10^6$-$1\times10^8$ cfu/ml and glucose @ 0.2 g/100 ml supernatant was added in the supernatant and incubated at 37-43° C. for about 17 hours. *Lactobacillus acidophilus* NCDC No 016 was procured from National Collection of Daily Cultures (NCDC) Dairy Microbiology Division, ICAR-National Dairy Research Institute, Karnal-132001, Haryana, India on Sep. 20, 2019. The precipitated protein was collected and was spray dried. The extraction and precipitation process were repeated with left over residue with similar process parameters. About 312.0 gm protein isolates was obtained. In order to recover un-precipitated proteins (about 40 g) of spent supernatant (obtained after precipitation of proteins), it may be concentrated up to 12-14% solid content using ultra-filtration (10 kDa) and spray dried at Inlet temperature 180° C., atomizing pressure 2.5 bar, outlet temperature 90° C. and Blower speed 2300 rpm. About 33.0 gm protein isolates was obtained using ultra-filtration. Hence, the process of the present disclosure provides a total of about 345 gm of protein isolates powder having protein content 90.0 g protein/100 gm.

Example 2

This example illustrates the preparation of a protein isolate from solvent extracted soyabean meal in accordance with one embodiment of the invention using the procedure of FIG. 1.

One kg hexane extracted untoasted soy meal. (Protein 50.0 g/100 g soy meal) is mixed with 10 litre of potable water. The mixture was stirred for about 80 minutes at about 70° C. to form slurry. The slurry was centrifuged at about 4000 g for about 20 minutes and supernatant was collected (8.5 litre). Microbial culture broth comprising *Lactobacillus fermentum* BBE4 and *Lactobacillus acidophilus* NCDC No 016 @ 1 ml/100 ml supernatant containing $1\times10^6$-$1\times10^8$ cfu/ml was added in the supernatant and incubated at a temperature of about 37-43° C. for about 5 hours. The precipitated protein was collected and was spray dried. The extraction and precipitation process were repeated with left over residue with similar process parameters. In order to recover un-precipitated proteins of spent supernatant (obtained after precipitation of proteins), it may be concentrated up to 12-14% solid content using ultra-filtration (10 kDa) and spray dried. Both obtained protein isolate powder is mixed to get total quantity. The mixture contains 90.0 g protein/100 g. The process is purely chemical free.

The invention claimed is:

1. A microbial process for preparation of a protein isolate or a protein concentrate from a de-oiled meal or a de-oiled flour, the microbial process comprising:
    adding potable water to the de-oiled meal or the de-oiled flour to form a first slurry;
    stirring the first slurry at a temperature in a range of 30° C. to 70° C. for 1 to 2 hours followed by centrifugation to obtain a first supernatant and a first residual cake;
    adding the potable water to the first residual cake to form a second slurry and stirring the second slurry at a temperature in a range of 30° C. to 70° C. for 1 to 2 hours, followed by centrifugation to obtain a second supernatant and a second residual cake;
    adding a microbial culture and a nutrient media to the first and the second supernatant and incubating at a temperature in a range of 37° C. to 43° C. for 10 to 20 hours in an incubator or a fermenter to precipitate the protein, wherein the microbial culture comprises *Lactobacillus fermentum* MTCC 12061 and *Lactobacillus acidophilus* NCDC 016;
    centrifuging to recover a precipitated protein and a spent supernatant; and drying the precipitated protein to obtain the protein isolate or the protein concentrate, wherein the protein isolate, has a protein content of at least 90% on dry basis.

2. The microbial process as claimed in claim 1, further comprising adding a salt and a base to the first slurry and adjusting a pH of the first slurry in a range of 9 to 10.

3. The microbial process as claimed in claim 1, wherein the centrifugation is carried out at a speed of 6000-8000 rpm for 10-30 minutes.

4. The microbial process as claimed in claim 1, wherein the microbial culture comprises *Lactobacillus fermentum* MTCC 12061 and *Lactobacillus acidophilus* NCDC 016 in a concentration range of $1\times10^6$-$1\times10^8$ cfu/ml.

5. The microbial process as claimed in claim 1, further comprising recovering un-precipitated proteins by ultra-filtration and spray drying, wherein the un-precipitated proteins are present in the spent supernatant, and wherein the un-precipitated proteins are concentrated up to 12-14% solid content.

6. The microbial process as claimed in claim 1, further comprising using the spent supernatant as an inoculum of the microbial culture.

7. The microbial process as claimed in claim 1, wherein the de-oiled meal or the de-oiled flour is derived from a protein source of a plant or an animal origin, wherein the protein source of the plant comprises an oil seed, wherein the oilseed is groundnut, soybean, sunflower, mustard, or sesame.

8. The microbial process as claimed in claim 1, wherein the protein isolate or the protein concentrate is a dried proteinaceous powder.

9. The microbial process as claimed in claim 8, wherein the dried proteinaceous powder is a probiotic protein powder.

10. The microbial process as claimed in claim 1, wherein the protein isolate or the protein concentrate has a lower anti-nutritional factor, wherein the lower anti-nutritional factor is trypsin inhibitor, or phytic acid.

11. The microbial process as claimed in claim 1, wherein the protein isolate or the protein concentrate has a water solubility of 45% at 20° C., wherein the protein isolate has a water solubility of 68% at 40° C., and wherein the protein isolate has a water solubility of 75% at 60° C.

12. A microbial process for preparation of a protein isolate or a protein concentrate from a de-oiled meal or a de-oiled flour, the microbial process comprising:
  adding water to the de-oiled meal or the de-oiled flour to form a slurry;
  stirring the slurry at a temperature in a range of 30° C. to 70° C. for 1 to 2 hours followed by centrifugation to obtain a supernatant and a residual cake;
  adding a microbial culture and a nutrient media to the supernatant and incubating at a temperature in a range of 37° C. to 43° C. for 10 to 20 hours to precipitate the protein, wherein the microbial culture comprises *Lactobacillus fermentum* MTCC 12061 and *Lactobacillus acidophilus* NCDC 016;
  centrifuging to recover a precipitated protein and a spent supernatant; and
  drying the precipitated protein to obtain protein isolate or the protein concentrate.

* * * * *